United States Patent [19]

Warriner

[11] Patent Number: Plant 7,717

[45] Date of Patent: Nov. 26, 1991

[54] ROSE PLANT JACORAL

[75] Inventor: William A. Warriner, Tustin, Calif.

[73] Assignee: Bear Creek Gardens, Inc., Medford, Oreg.

[21] Appl. No.: 512,990

[22] Filed: Apr. 23, 1990

[51] Int. Cl.[5] ..... A01H 5/00

[52] U.S. Cl. ..... Plt./9

[58] Field of Search ..... Plt. 7, 9

[56] References Cited

U.S. PATENT DOCUMENTS

Plt. 2,292 10/1963 Morey, Jr. ..... Plt. 9

*Primary Examiner*—Howard J. Locker

*Attorney, Agent, or Firm*—Klarquist, Sparkman, Campbell, Leigh & Whinston

[57] ABSTRACT

A miniature class rose plant having dwarf upright habit of growth, pink flowers having a darker pink center, and dark green glossy foliage.

1 Drawing Sheet

The present invention relates to a new and distinct variety of rose plant of the miniature class which was originated by me by crossing the variety Merci U.S. Plant Pat. No. 3,144, with the variety Party Girl U.S. Plant Pat. No. 4,598.

The primary objective of this breeding was to produce a new rose variety having the miniature habit and soft flower color of the male parent, Party Girl, coupled with the dark leathery foliage of the female parent, Merci. The objective was substantially achieved along with other desirable improvements as evidenced by the following unique combination of characteristics which are outstanding in the new variety and which distinguish it from its parents as well as from all other varieties of which I am aware:

1. Dwarf upright habit of growth.
2. Pink flowers with a darker pink center.
3. Dark green glossy foliage.

Asexual reproduction of this new variety by budding, as performed at Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with The Royal Horticultural Society (London) Colour Chart except where ordinary dictionary significance of color is indicated.

Parentage:

*Seed parent.*—Merci.

*Pollen parent.*—Party Girl.

Classification:

*Botanical.*—Rosa hybrida.

*Commercial.*—Miniature.

FLOWER

Observations made from specimens grown in a garden in Somis, Calif., from June to October, 1989.

Blooming habit: Recurrent.

Bud:

*Size.*—About ½ inch long when the petals start to unfurl.

*Form.*—The bud form is short, pointed ovoid.

*Color.*—When sepals first divide, the bud color is Red Group 49B. When half blown, the upper and lower sides of the petals are Red Group 49B with some fading at the flower edges to 49C.

*Sepals.*—Color: Green Group 138B. Surface texture: Covered with fine hairs. There are three normally appendaged sepals. There are two unappendaged sepals with hairy edges.

*Receptacle.*—Color: Bronze and green. Shape: Funnel. Size: Broad, medium. Surface: Smooth.

*Peduncle.*—Length: Short, averaging about ½ to ¾ inch. Surface: Smooth. Color: Bronzy. Strength: Stiff, erect.

Bloom:

*Size.*—Small. Average open diameter is 1 inch.

*Borne.*—Singly and several together, in clusters having pyramidal shape.

*Stems.*—Short, strong.

*Form.*—When first open, bloom is cupped. Bloom flattens as it opens, with outer petals curling back, in a quill fashion.

*Petalage.*—Number of petals under normal conditions: 25–30.

*Color.*—The upper and reverse sides of the petals are Red Group 49B fading the Red Group 49D at petal edges. The base of petals has a small greenish white half moon at the point of attachment. The major color on the upper side is Red Group 49B to D, the petals at the center of the flower being colored Red Group 50B.

*Variegations.*—None.

*Discoloration.*—No general tonality change at the end of the first day. At the end of the third day, fading to Red Group 49D, except at the center of the flower.

*Fragrance.*—Slight.

Petals:

*Texture.*—Thin.

*Shape.*—Deltoid.

*Form.*—Tips slightly recurved, edges slightly quilled.

*Arrangement.*—Imbricated, with few petaloids in the center.

*Persistence.*—Petals drop off cleanly.

*Lastingness.*—On the plant: Fair, about 3 to 5 days. As a cut flower: Fair, about 3 to 5 days.

Reproductive parts:

*Anthers.*—Size: Large. Quantity: Many. Color: Reddish brown. Arrangement: Regular around styles, mixed with occasional petaloids.

*Filaments.*—Color: Reddish brown.

*Pollen.*—Color: Gold yellow, darkening quickly.

*Styles.*—Color: Reddish.

*Stigmas.*—Color Red.

Plant form: Bush.

Plant growth: Very vigorous, dwarf, upright, compact. The plant at maturity is about 14 inches tall and 10 inches wide.

Foliage: Number of leaflets on normal mid-stem leaves: 5.

*Size.*—Small, less than about 1½ inches long.

*Quantity.*—Normal.

*Color.*—New foliage: Reddish. Old foliage: Green Group 137A, glossy.

Leaflets:

*Shape.*—Pointed oval.

*Texture.*—Upper side: Semi glossy, smooth.

*Edge.*—Serrated.

*Serration.*—Single, small.

*Petiole rachis.*—Color: Reddish.

*Petiole underside.*—Rough, with prickles.

*Stipules.*—Medium, bearded.

*Disease resistance.*—Susceptible to mildew and blackspot under normal growing conditions at Somis, Calif.

Wood:

*New wood.*—Color: Reddish. Bark: Smooth.

*Old wood.*—Color: Green. Bark: smooth.

Prickles:

*Quantity.*—Ordinary quantity on main canes from base and on laterals from main canes.

*Form.*—Straight to hooked slightly downward.

*Color when young.*—Red.

Small prickles:

*Quantity.*—Few on main stalks and on laterals.

*Color.*—Green.

I claim:

1. A new and distinct variety of rose plant of the miniature class, substantially as herein shown and described, characterized particularly as to novelty by the unique combination of its dwarf upright habit of growth, dark green glossy foliage, and unusual pink flower color with darker pink at the center.

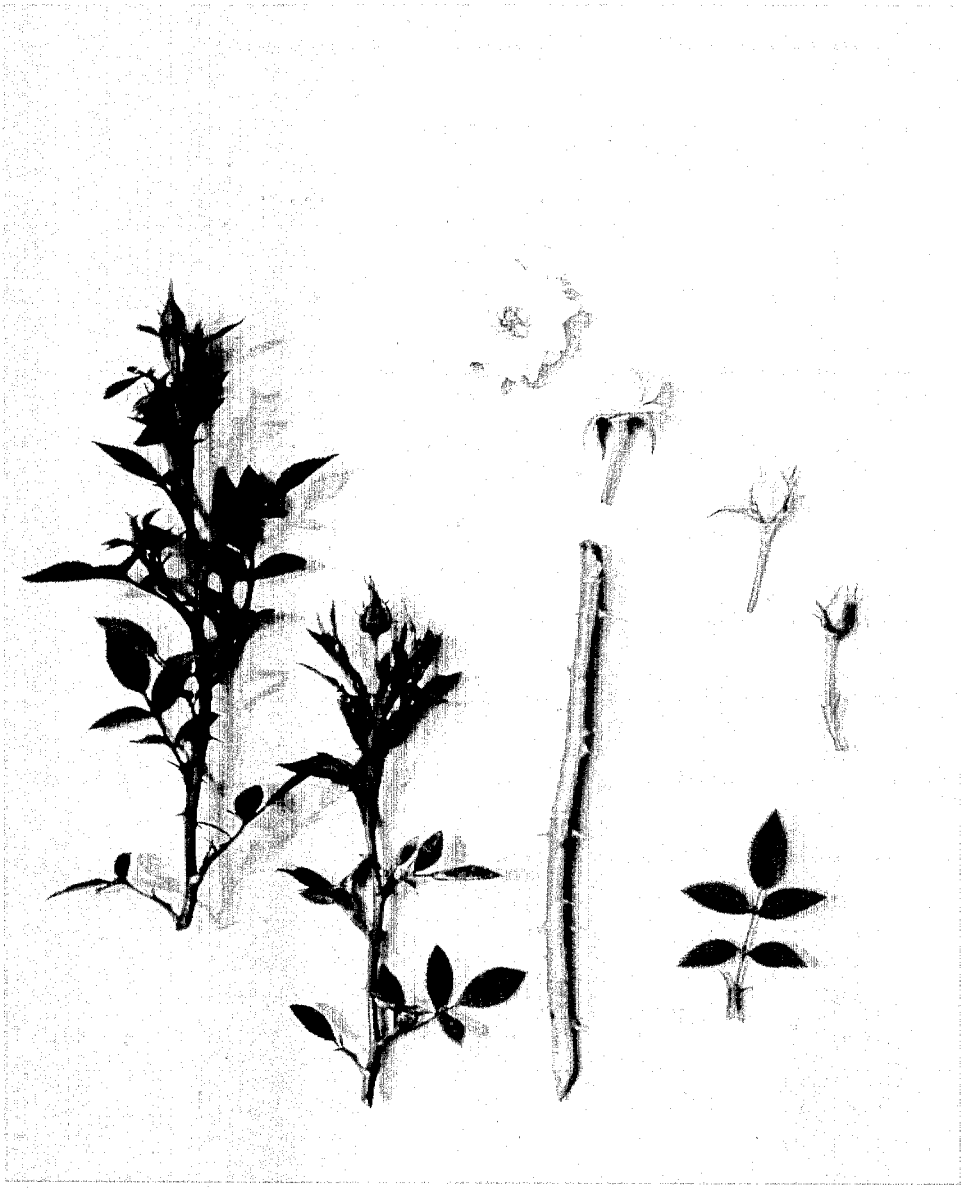

* * * * *